(12) United States Patent
Gross et al.

(10) Patent No.: US 9,358,135 B2
(45) Date of Patent: Jun. 7, 2016

(54) DEVICES, METHODS AND SYSTEMS FOR HYDRATING A MEDICAL IMPLANT MATERIAL

(75) Inventors: Jeffrey M. Gross, Memphis, TN (US);
William F. McKay, Memphis, TN (US);
Jeffrey L. Scifert, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2082 days.

(21) Appl. No.: 11/787,631

(22) Filed: Apr. 17, 2007

(65) Prior Publication Data
US 2008/0260598 A1    Oct. 23, 2008

(51) Int. Cl.
*A61F 2/46*     (2006.01)
*B65D 25/08*  (2006.01)
*A61B 17/00*    (2006.01)
*A61F 2/30*     (2006.01)

(52) U.S. Cl.
CPC .............. *A61F 2/4644* (2013.01); *B65D 25/08* (2013.01); *A61B 2017/00969* (2013.01); *A61F 2002/30291* (2013.01); *A61F 2002/30601* (2013.01); *A61F 2002/4685* (2013.01); *A61F 2002/4693* (2013.01); *A61F 2230/0091* (2013.01)

(58) Field of Classification Search
CPC .. A61L 2430/40; A61F 2/0095; C12M 23/12; C12M 23/02
USPC .................. 604/82, 84, 85; 206/219, 221; 606/92–94
See application file for complete search history.

(56) References Cited

U.S. PATENT DOCUMENTS

| | | | | |
|---|---|---|---|---|
| 3,745,091 A * | 7/1973 | McCormick | ............... | 435/305.3 |
| 4,458,733 A * | 7/1984 | Lyons | .................. | A61J 1/2089 141/1 |
| 4,467,588 A * | 8/1984 | Carveth | ............... | A61J 1/2093 206/219 |
| 4,994,056 A * | 2/1991 | Ikeda | ............................ | 604/410 |
| 5,385,546 A * | 1/1995 | Kriesel | ................. | A61J 1/2089 604/411 |
| 5,490,736 A * | 2/1996 | Haber et al. | .................... | 401/40 |
| 5,951,160 A * | 9/1999 | Ronk | ............................. | 366/130 |
| 6,286,670 B1 * | 9/2001 | Smith | .......................... | 206/221 |
| 6,517,526 B1 * | 2/2003 | Tamari | ................ | A01N 1/0236 604/403 |

(Continued)

OTHER PUBLICATIONS

Collins English Dictionary, Capillary. Accessed online Dec. 27, 2013.*

*Primary Examiner* — Kami A Bosworth
*Assistant Examiner* — Matthew A Engel
(74) *Attorney, Agent, or Firm* — Sorell Lenna & Schmidt LLP

(57) ABSTRACT

Devices for hydrating materials, such as, for example, medical implant materials include a container body defining therein a hydration chamber. A barrier separates the chamber into a material holding area and a hydrating fluid bay and defines at least one aperture and is configured to allow passage of hydrating fluid from the hydrating fluid bay to the material holding area. In some embodiments, devices provided by the present application are operable for use in hydrating and delivering a material.

10 Claims, 7 Drawing Sheets

(56) References Cited

U.S. PATENT DOCUMENTS

| | | | |
|---|---|---|---|
| 6,533,817 B1* | 3/2003 | Norton et al. | 623/17.16 |
| 6,610,026 B2 | 8/2003 | Cragg et al. | |
| 6,648,133 B1* | 11/2003 | Blaschke | A61F 2/0095 |
| | | | 206/221 |
| 6,904,701 B2* | 6/2005 | Htoo | F26B 5/06 |
| | | | 34/235 |
| 6,953,465 B2 | 10/2005 | Dieck et al. | |
| 6,991,096 B2 | 1/2006 | Gottlieb et al. | |
| 7,172,071 B2* | 2/2007 | Hawkins | A61F 2/4601 |
| | | | 206/366 |
| 7,198,150 B1* | 4/2007 | Blaschke | A61F 2/0095 |
| | | | 206/221 |
| 7,422,726 B2* | 9/2008 | Hammerstedt | A01N 1/02 |
| | | | 34/284 |
| 7,445,633 B2* | 11/2008 | Hoerger | A61F 2/4644 |
| | | | 366/139 |
| 7,789,854 B2* | 9/2010 | Talamonti | A01N 25/34 |
| | | | 604/416 |
| 8,449,520 B2* | 5/2013 | Pepper | A61B 19/0248 |
| | | | 34/284 |
| 2002/0049405 A1* | 4/2002 | Deslauriers et al. | 604/82 |
| 2004/0081588 A1* | 4/2004 | Hammerstedt | A01N 1/02 |
| | | | 422/550 |
| 2004/0098024 A1 | 5/2004 | Dieck et al. | |
| 2005/0087457 A1* | 4/2005 | Schmidt et al. | 206/219 |
| 2007/0074980 A1* | 4/2007 | Bankoski et al. | 206/219 |
| 2007/0118068 A1* | 5/2007 | Hawkins | 604/19 |
| 2007/0138033 A1* | 6/2007 | Cho | 206/219 |
| 2007/0209951 A1* | 9/2007 | Okahisa | 206/219 |
| 2008/0003145 A1* | 1/2008 | Nurse | B01L 3/502738 |
| | | | 422/400 |
| 2009/0325295 A1* | 12/2009 | Masini | C12M 21/08 |
| | | | 435/377 |
| 2010/0155282 A1* | 6/2010 | Govil | A61F 2/0095 |
| | | | 206/438 |

* cited by examiner

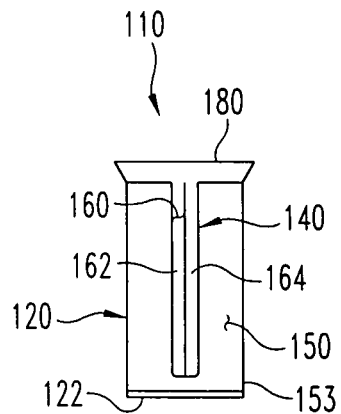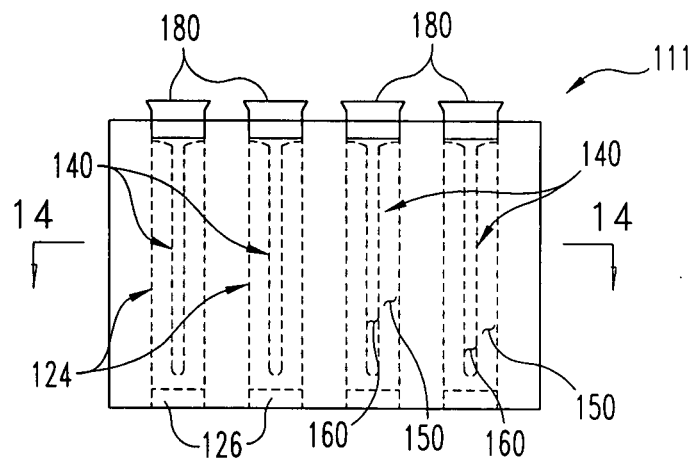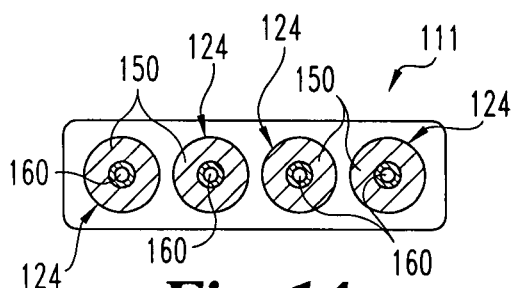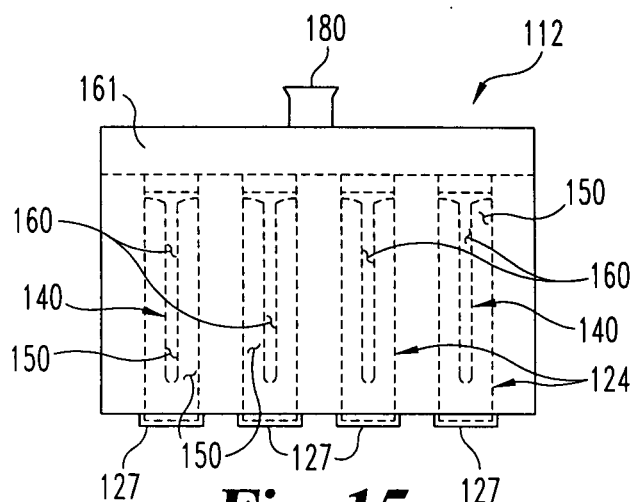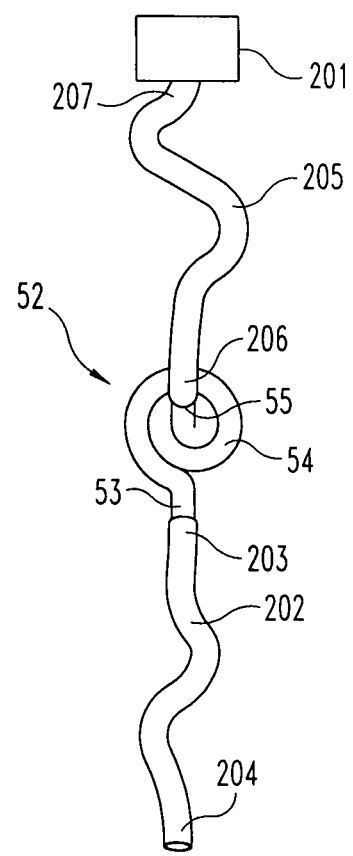

DEVICES, METHODS AND SYSTEMS FOR HYDRATING A MEDICAL IMPLANT MATERIAL

BACKGROUND

The present application relates to the field of biomedical implant materials and, in particular, devices, methods and systems for hydrating implantable materials, such as allograft materials, xenograft materials and synthetic materials, to prepare the materials for implant.

Various types of implant materials are provided commercially in a dehydrated form and are hydrated a short time before implantation into an in vivo location. For example, in order to preserve the useful shelf life of allograft tissue, as well as to inhibit bacterial growth within the allograft tissue, it is common to dehydrate the allograft tissue, for example by freeze drying. Freeze-drying quickly removes all or nearly all of the moisture within the allograft tissue, thus inhibiting any subsequent bacterial growth. Then, prior to employing the allograft tissue in a surgical setting, it is generally necessary to re-hydrate the freeze-dried allograft tissue with a fluid such as sterilized water, saline or the like.

Hydration of an allograft material or other type of material is typically a cumbersome process that exposes the freeze-dried allograft tissue to atmospheric pathogens during the re-hydration process. Also, the process is often done in a manner that does not ensure that the liquid material thoroughly infuses into the pores of the allograft material. Moreover, the handling of the materials after hydration, and the delivery of such hydrated materials to an in vivo location also present difficulties. The same types of problems are also encountered with regard to the use of xenograft materials and synthetic materials that are used as medical implants.

It is apparent from the above that there is a continuing need for advancements in the relevant field, including new devices and new methods for hydrating medical implant materials and for delivering the hydrated materials to in vivo locations. The present application addresses this need and provides a variety of additional benefits and advantages.

BRIEF DESCRIPTION OF THE DRAWINGS

FIG. 12 is a diagrammatic front section view of another embodiment of a hydration device in accordance with the present application.

FIG. 13 is a front elevation view of another embodiment of a hydration device in accordance with the present application with some elements shown in phantom.

FIG. 14 is a cross section of the embodiment depicted in FIG. 13 taken at line 14-14.

FIG. 15 is a is a front elevation view of another embodiment of a hydration device in accordance with the present application with some elements shown in phantom front elevation view of another embodiment of a hydration device in accordance with the present application with some elements shown in phantom.

FIG. 16 is a perspective view of an assembly for delivering a flowable hydrated material to an in vivo location in accordance with the present application.

SUMMARY

Figure 1:
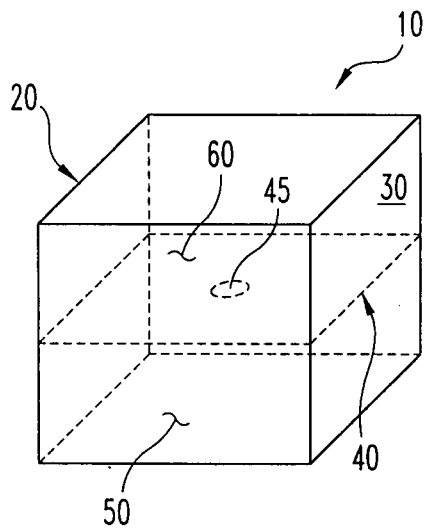
FIG. 1 is a diagrammatic perspective view of one embodiment of a hydration device in accordance with the present application.

The present application involves devices, methods and systems for hydrating materials, such as, for example, medical implant materials. In some embodiments, devices provided by the present application are operable for use in hydrating and delivering a material.

In one aspect of the application there is provided a device for hydrating a medical implant material that includes a container body defining therein a hydration chamber and a barrier positioned in the hydration chamber. The barrier separates the chamber into a material holding area and a hydrating fluid bay. The barrier defines at least one aperture and is configured to allow passage of hydrating fluid from the hydrating fluid bay to the material holding area. In one embodiment, the barrier defines a plurality of apertures through which the material holding area fluidly communicates with the hydrating fluid bay. In one example, the apertures can be of a type that are effective to allow passage of fluid therethrough upon application of a threshold pressure gradient across the barrier. In another example, the apertures can be of a type that allow fluid to passes through the barrier by diffusion. In exemplary alternative embodiments, the barrier comprises a member selected from the group consisting of a permeable element, a screen and a fabric. With regard to possible shapes of the barrier, in one embodiment, the barrier comprises a permeable probe-like barrier defining an internal hydrating fluid bay and configured to extend into the material holding area. The probe-like barrier can optionally include a portion that is impermeable to the hydrating fluid and a portion that is permeable. The probe-like barrier can be tubular, and can optionally be configured to be rotated.

In another embodiment, the hydrating device further includes a seal that is effective to prevent passage of a hydrating fluid from the hydrating fluid bay to the material holding area until the seal is punctured or moved from at least a portion of the barrier. The seal can comprise, for example, a membrane adjacent the barrier.

In yet another embodiment, the device further includes a connection port in fluid communication with the hydrating fluid bay, the port configured for engagement with a hydrating fluid source. For example, the connection port can comprise a Luer connector. Moreover, the connection port can optionally include a valve. In other embodiments, the device also includes a valve in fluid communication with the material holding area. An exemplary fluid source that can be used to introduce fluid into the hydrating fluid bay is a fluid-filled syringe.

In another embodiment, the container body comprises first and second portions configured for alternate engagement with one another to form the hydration chamber and disengagement from one another for removal of a material from the material holding area. The container body can further include a gasket between the first and second portions to provide a seal when the first and second portions are in an engaged position. The container body can also optionally include a hinge connected to the first and second portions.

In still another embodiment, the device has contained in the material holding area a delivery device that itself contains a material to be hydrated. The delivery device can be, for example, a coil delivery device or a straight tube. In addition, the delivery device can comprise a multi-chamber cartridge. One exemplary multi-chamber cartridge is a revolving cartridge. Another exemplary multi-chamber cartridge is a cartridge with linearly arranged tubular chambers.

In still yet another embodiment, the device is effective to hydrate a flowable material and the container body is configured to deliver the material to an in vivo location. The container body can be configured for attachment to a delivery device for direct delivery of the material to an in vivo location. The container body can be, for example, a coil delivery device. In addition, the material holding area can be formed to function as a material delivery vehicle, and the material holding area can itself comprise a coiled delivery device. Alternatively, the container body in one exemplary embodiment comprises a syringe. In one representative embodiment, the syringe defines a barrel that operates as the material holding area, and comprises a hydrating component releasably affixed to the barrel and comprising a connection port affixed to a probe-like barrier that extends into the barrel and defines an internal hydrating fluid bay. As discussed above, the probe-like barrier can optionally include a portion that is impermeable to the hydrating fluid and a portion that allows hydrating fluid to pass therethrough. Also, the probe-like barrier can be configured to be rotated.

As yet another alternative device that is effective to hydrate a flowable material and to deliver the material to an in vivo location, the container body can comprise a cartridge configured for engagement with an expresser device. A suitable expresser device in some embodiments is a syringe containing a fluid, the syringe being operable to apply hydraulic pressure to the material holding area to express the material from the material holding area. In other embodiments, the expresser device comprises a mechanical piston operable to apply mechanical pressure to the material holding area to express the material from the material holding area. The cartridge can have a single chamber, or can have a plurality of material holding areas for hydrating respective quantities of the material. With regard to cartridges having multiple chambers, in one embodiment, each of the plurality of material holding areas is separated from a respective one of a plurality of hydrating fluid bays by a respective one of a plurality of barriers. In another embodiment, each of the plurality of material holding areas is separated from a manifold hydrating fluid chamber by a barrier or by a respective one of a plurality of barriers. An exemplary multi-chamber device, the cartridge comprises a revolving-type cartridge.

In another aspect of the application a device for hydrating a medical implant material is provided that includes a container body defining therein a hydration chamber and a permeable probe-like barrier positioned in the hydration chamber. The barrier separates the chamber into an internal hydrating fluid bay and a material holding area external to the probe-like barrier. The barrier is configured to allow passage of hydrating fluid from the hydrating fluid bay to the material holding area. In one embodiment, the probe-like barrier comprises a portion that is impermeable to the hydrating fluid and a portion that is permeable. In another embodiment, the probe-like barrier is configured to be rotated. In yet another embodiment, the device further comprises a connection port in fluid communication with the hydrating fluid bay, the port configured for engagement with a hydrating fluid source. The connection port can comprise, for example, a Luer connector.

In yet another aspect, the application provides a device for hydrating multiple quantities of a medical implant material that includes a cartridge defining therein a plurality of hydration chambers and a plurality of permeable probe-like barriers. Each barrier is positioned in a respective one of the hydration chambers and separates the respective chamber into an internal hydrating fluid bay and a material holding area external to the probe-like barrier. The barrier is configured to allow passage of a hydrating fluid from the hydrating fluid bay to the material holding area. In one embodiment, the device further comprises a plurality of connection ports, each of said connection ports in fluid communication with a respective one of the plurality of hydrating fluid bays, each of the ports configured for engagement with a hydrating fluid source. In another embodiment, the cartridge is configured for engagement with an expresser device.

In still another aspect of the present application, there is provided a device for hydrating multiple quantities of a medical implant material that includes a cartridge defining therein a plurality of hydration chambers and a plurality of permeable probe-like barriers, wherein each barrier is positioned in a respective one of the hydration chambers and separates the respective chamber into an internal hydrating fluid bay and a material holding area external to the probe-like barrier, and wherein each of the hydrating fluid bays is in fluid communication with a manifold hydrating fluid chamber. The barrier is configured to allow passage of a hydrating fluid from the hydrating fluid bay to the material holding area.

Another aspect of the application provides a device for hydrating a medical implant material that includes a syringe having a barrel defining therein a hydration chamber and a permeable probe-like barrier positioned in the barrel. The barrier separates the chamber into an internal hydrating fluid bay and a material holding area external to the probe-like barrier. The probe-like barrier is configured to allow passage of hydrating fluid from the hydrating fluid bay to the material holding area, and the probe-like barrier has a connection port affixed thereto. In one embodiment, the barrier is removable to allow expression of the material from the barrel.

In another aspect of the application a packaged product is provided. The packaged product includes a container body defining therein a hydration chamber, an unhydrated medical material to be hydrated contained in the chamber, and a removable seal operable to prevent passage of moisture into contact with the medical material. Exemplary materials to be hydrated include an absorbable collagen sponge (ACS), a MasterGraft Matrix and a MasterGraft Putty. Exemplary hydrating fluids include blood, bone marrow, saline, water and a reconstituted recombinant protein solution. In one embodiment, the seal is positioned in the hydration chamber and separates the hydration chamber into a material holding area and a hydrating fluid bay; and the seal is operable to prevent passage of moisture from the hydrating fluid bay into the material holding area. In another embodiment, a hydrating fluid is contained in the hydrating fluid bay. In yet another embodiment, a water permeable barrier is positioned in the hydration chamber adjacent the seal. In still another embodiment, the barrier defines a plurality of apertures, such as, for example, capillary apertures, through which the material holding area fluidly communicates with the hydrating fluid bay. The product can further include a fluid port formed in the container body in fluid communication with the hydrating fluid bay and configured for engagement with a hydrating fluid source. The container body can include a removable or hinged lid to allow for introduction of the hydrating fluid before or after removal of the seal. The material to be hydrated can be contained within a delivery vehicle. For example, the implant delivery vehicle can comprise a coiled delivery device.

In yet another aspect, the present application provides a device for delivering a flowable, hydrated material to an in vivo location, the device including a retaining member configured to releasably engage a container body containing a flowable, hydrated material, an expresser component that is operable to express the material from the chamber, and a conduit that is operable to receive the material after it is expressed from the chamber. The device can be configured for use in connection with a container body that comprises a multi-chamber cartridge, such as, for example, a revolving cartridge defining a plurality of hydration chambers or a slidable cartridge defining a plurality of hydration chambers in linear relation to one another.

Yet another aspect of the invention provides a method for hydrating and delivering material to an in vivo location that includes: (1) providing a container body defining therein a tubular material holding area and a material to be hydrated contained therein; (2) passing a hydrating fluid into the material holding area to hydrate the material, thereby providing a flowable hydrating material; (3) affixing the container body to a device for delivering the flowable, hydrated material to an in vivo location, the device including a retaining member configured to releasably engage the container body, an expresser component that is operable to express the material from the material holding area, and a conduit that is operable to receive the material after it is expressed from the chamber; and (4) expressing the material from the material holding area and through the conduit to an in vivo location. The method can be employed using a container body that comprises a cartridge defining therein a plurality of hydration chambers, such as, for example, a revolving cartridge defining a plurality of hydration chambers or a slidable cartridge defining a plurality of hydration chambers in linear relation to one another. In one manner of practicing the method, the respective components have internal dimensions corresponding to one another in certain ratios. For example, in one embodiment, the material holding area has a first internal diameter, the conduit has a second internal diameter and the second diameter is within a range that is no more than 50% larger or smaller than the first diameter. In another embodiment, the second diameter is substantially the same as the first diameter. In yet another embodiment, the assembled container body and delivering device is operable to deliver a material having a viscosity of from 700 to about $1.0 \times 10^8$ centi-Poise (cP) at a temperature of from about 22° C. to about 25° C.

In another aspect of the application there is provided a method for delivering a flowable hydrated material to an in vivo location that includes: (1) providing a container defining therein a tubular material holding area and containing a flowable hydrated material in the tubular material holding area; (2) affixing a source of hydraulic pressure to a first end of the tubular material holding area; and (3) transmitting hydraulic pressure from the source to the first end of the tubular material holding area to express the material from an opposite second end of the tubular material holding area. In one manner of practicing the method, the source of hydraulic pressure is a syringe. In another embodiment, a first conduit is positioned between the source the first end of the tubular material holding area, and is operable to transmit hydraulic pressure from the source through the first conduit to the first end of the tubular material holding area. In yet another embodiment, a second delivery conduit is attached to the second end of the tubular material holding area for delivery of the material from the material holding area to an in vivo location. The tubular material holding area can have a coiled configuration, a straight tube configuration or other configurations.

In still another aspect, the application provides a method for hydrating a medical implant material for use as a medical implant that includes: (1) providing a hydration device including a container body defining therein a hydration chamber; a barrier positioned in the hydration chamber, the barrier operable to separate the chamber into a material holding area and a hydrating fluid bay and to allow passage of hydrating fluid from the hydrating fluid bay to the material holding area; and a removable seal effective to prevent passage of a hydrating fluid from the hydrating fluid bay to the material holding area until the seal is punctured or moved from at least a portion of the barrier; (2) providing a prehydrated material in the material holding area; (3) providing a hydrating fluid in the hydrating fluid bay; and (4) breaching the seal to allow passage of the hydrating fluid from the hydrating fluid bay to the material holding area for hydrating the medical implant material.

Further embodiments, forms, features and aspects of the present application shall become apparent from the detailed description and figures provided herewith.

DETAILED DESCRIPTION OF SELECTED EMBODIMENTS

For the purposes of promoting an understanding of the principles of the inventions described herein, reference will now be made to the embodiments illustrated in the drawings and specific language will be used to describe the same. It will nevertheless be understood that no limitation of the scope of any invention is thereby intended. Any alterations and further modifications in the illustrated embodiments, and any further applications of the principles described and illustrated herein are contemplated as would normally occur to one skilled in the art.

With reference to FIG. 1, device 10 is operable to hydrate a medical implant material. Device 10 includes container body 20 defining therein hydration chamber 30. Barrier 40 is positioned in hydration chamber 30 and separates hydration chamber 30 into material holding area 50 and hydrating fluid bay 60. Aperture 45 in barrier 40 is configured to allow passage of a hydrating fluid from hydrating fluid bay 60 to material holding area 50. In one embodiment, body 20 is composed of a rigid material such as, for example, a rigid plastic material.

Figure 2:
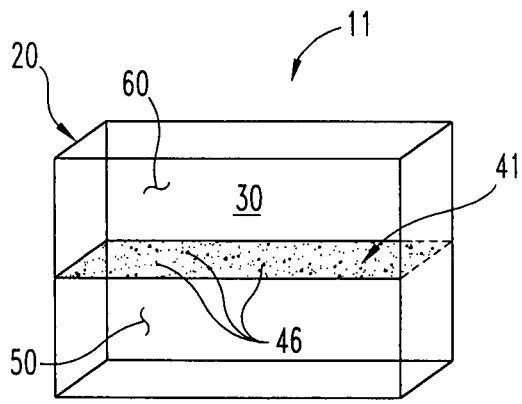
FIG. 2 is a diagrammatic perspective, cross sectional view of another embodiment of a hydration device in accordance with the present application.

In another embodiment, depicted in FIG. 2, device 11 includes barrier 41 that defines a plurality of apertures 46 through which material holding area 50 fluidly communicates with hydrating fluid bay 60. Apertures 46 can be of a type, for example, that allow for ready flow of hydrating fluid (not shown) therethrough when hydrating fluid is introduced into hydrating fluid bay 60. In another embodiment, apertures 46 are effective to allow passage of a hydrating fluid therethrough only upon application of a threshold pressure gradient across the barrier. For example, apertures can be capillary apertures that restrict passage of a hydrating fluid under normal conditions, but then permit passage of the fluid when a positive pressure is applied to hydrating fluid bay 60 or a negative pressure is applied to material holding area 50. In alternative embodiments, barrier 41 can be formed of a permeable element, such as, for example, a porous plastic element, a screen or a fabric.

Figure 3:
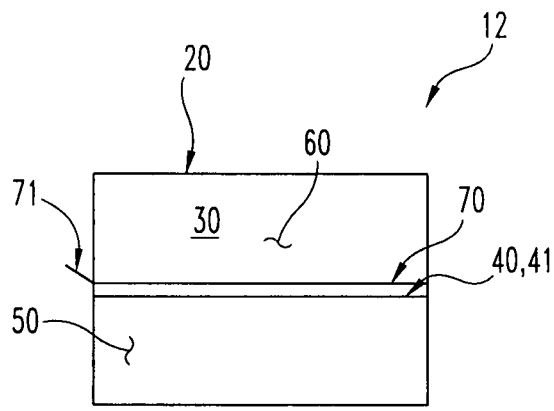
FIG. 3 is a diagrammatic front elevation view of another embodiment of a hydration device in accordance with the present application.

In another embodiment, depicted in FIG. 3, device 12 for hydrating a medical implant material includes removable seal 70. In the embodiment shown, seal 70 is positioned adjacent barrier 40, 41. Seal 70 is effective to prevent passage of a hydrating fluid from hydrating fluid bay 60 to material holding area 50 until seal 70 is punctured or moved from at least a portion of barrier 40, 41. For example, in one embodiment, seal 70 is a membrane positioned adjacent barrier 40, 41, that is effective to prevent passage of a hydrating fluid from hydrating fluid bay 60 to material holding area 50 until seal 70 is punctured or moved from at least a portion of the barrier. Seal 70 can be moved or punctured in a variety of ways. For example, in one embodiment, seal can be punctured by application of a threshold pressure on a fluid (not shown) present in hydrating fluid bay 60. In another embodiment, seal is connected to optional tab 71 external to container 20. Tab 71 is configured such that a pulling action on tab 71 operates to move seal 70 In one embodiment, seal 70 and tab 71 are of a type that can be pulled entirely free of device 12 upon application of a pulling force on tab 71. In another embodiment, container includes an externally actuated puncture device (not shown) for manually puncturing the seal when hydration of the material is desired.

In the embodiment depicted in FIG. 3, seal 70 is positioned on the hydrating fluid bay 60 side of barrier 40, 41; however, it is to be understood that seal 70 can be positioned in different locations in other embodiments. For example, seal 70 can be positioned on the material holding area 50 side of barrier 40, 41 or in locations separated from barrier 40, 41, as long as seal 70 is positioned to separate a material (not shown) positioned in material holding area 50 from a hydrating fluid to prevent premature hydration of the material.

Figure 4:
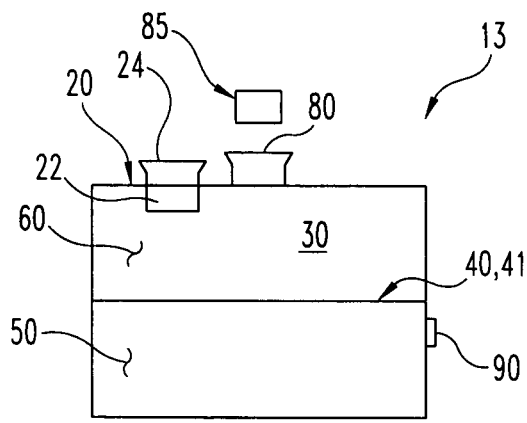
FIG. 4 is a diagrammatic front elevation view of another embodiment of a hydration device in accordance with the present application.

With reference to FIG. 4, device 13 includes connection port 80 in fluid communication with hydrating fluid bay 60. Port 80 is configured for engagement with a hydrating fluid source 85. The fluid source can be, for example, a fluid-filled syringe. In certain embodiments, port 80 includes a female Luer connector for mating with a syringe or like fluid source equipped with a male Luer connector. In one embodiment, port 80 operates as a seal until a fluid source is engaged thereto, at which time port 80 permits hydrating fluid to pass therethrough into hydrating fluid bay 60. As will be appreciated by a person skilled in the art, a variety of Luer connector geometries are known and can be employed to introduce a hydrating fluid into chamber 60. For example, Luer connector devices are known in which the female Luer connector operates as, or is coupled to, a valve, which prevents passage of fluid therethrough until a corresponding male Luer connector is seated therein. In certain embodiments, for example, the valve is a one-way valve that permits flow of a fluid into chamber 60 but not out of chamber 60. In other embodiments, the valve is of a type that is actuated by engagement of a corresponding male Luer connector. Port 80 can also include connection means (not shown), such as for example, a threaded surface, for sealingly and removably engaging a hydrating fluid source thereto. These and other embodiments are contemplated by the present application.

In an embodiment having a port such as port 80 shown in FIG. 4 and a seal such as seal 70 shown in FIG. 3, introduction of hydrating fluid into hydrating fluid bay 60 does not begin a hydration process as long as seal 70 remains in place and operable to keep the hydrating fluid separated from a material positioned in area 50. In such an embodiment, hydrating fluid can be introduced in advance of a time when it is desired to initiate hydration of a material, and the hydration process can be later initiated by removal or puncturing of the seal. Alternatively, it is possible to use such an embodiment by first removing the seal, and then infusing a hydrating fluid into the hydrating fluid bay, which will result in passage of the fluid into contact with a material held in material holding area 50.

The present application contemplates that hydrating fluid placed in bay 60 passes through barrier 40, 41 through apertures 45, 46 by diffusion, by gravity flow, in response to a pressure gradient, or by other mechanisms. In an embodiment having a port such as port 80 shown in FIG. 4 and a barrier 41 as depicted in FIG. 2 that has a plurality of capillary apertures, a hydration process can be initiated by introducing a hydrating fluid into hydrating fluid bay 60 through port 80 and then applying a pressure gradient across barrier 41 to pass the hydrating fluid from the hydrating fluid bay to the material holding area. When movement of the hydrating fluid is to be achieved by establishment of a pressure gradient, the gradient can be established by exerting a positive pressure on hydrating fluid bay 60, by exerting a negative pressure on material holding area 50, or both. With regard to the former, pressure in hydrating fluid bay 60 can be increased hydraulically, for example, by introducing additional hydrating fluid into hydrating fluid bay 60 through the port after the hydrating fluid has been introduced into bay 60, thereby exerting a positive pressure on the hydrating fluid. Alternatively, pressure in hydrating fluid bay 60 can be increased hydraulically by introducing a gas into hydrating fluid bay 60 under positive pressure through port 80. Pressure can alternatively be applied to bay using other mechanisms, such as, for example, using optional mechanical pressure applicator 22 positioned in bay 60. Pressure applicator 22 can be, for example, a hydraulically-actuated piston or a hydraulically-inflatable bladder. Optional port 24 is operable to communicate hydraulic pressure from a hydraulic pressure source (not shown) to pressure applicator 22. Alternatively, pressure applicator 22 can be actuated using other means connected thereto or remote therefrom as would occur to a person of ordinary skill in the art.

Device 13 can also optionally include valve 90 that fluidly communicates with material holding area 50. In one embodiment, valve 90 is a pressure release valve. When a pressure gradient is used to move hydrating fluid from bay 60 into area 50, movement of the hydrating fluid is aided by releasing pressure from bay 50. Absent a release of pressure, any air or other gas present in area 50 would inhibit the establishment of a suitable pressure gradient, and inhibit the passage of fluid into area 50. By releasing pressure through valve 90, however, a suitable pressure gradient can be achieved by applying a positive pressure to bay 60 that is greater than the pressure at which valve 90 opens to release fluids from area 50. A wide variety of pressure release valves that can be selected for use in connection with this embodiment are well known and readily available commercially.

In another embodiment, valve 90 is configured for attachment of a source of vacuum (not shown) for reducing the pressure in area 50. A vacuum source can be used, for example, after hydrating fluid is introduced into bay 60 to draw the hydrating fluid into contact with a material to be hydrated (not shown) in area 50. Alternatively, a vacuum source could be used to withdraw gases from hydration chamber 30 before a hydrating fluid is introduced into bay 60. It is to be further understood that valve 90 can be omitted, and would not be needed for certain uses of device 13. For example, a material to be hydrated could be packaged in device 13 in a vacuum-sealed arrangement, i.e., using a packaging process by which gases are removed from bay 60 and area 50 after placement of a material to be hydrated in area 50. In such an embodiment, valve 90 can be omitted.

Figure 5:
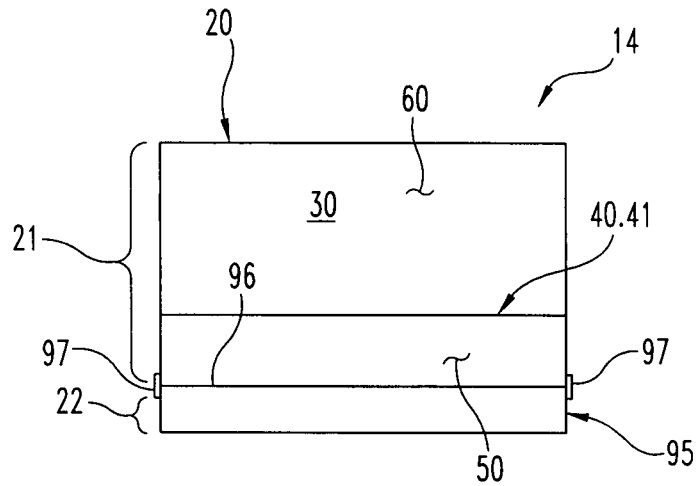
FIG. 5 is a diagrammatic front elevation view of another embodiment of a hydration device in accordance with the present application.

With reference to FIG. 5, container body 20 of device 14 includes first portion 21 and second portion 22 that are separable from one another for accessing hydration chamber 30. More particularly, portions 21 and 22 are configured for alternate engagement with one another to form the hydration chamber and disengagement from one another for placing a material in material holding area 50 or for removing a material from material holding area 50. In the embodiment shown in FIG. 5, the junction of portions 21 and 22 is in the portion of the container that defines material holding area 50; however, it is also contemplates that the junction can alternatively be in the portion of the container that defines hydrating fluid bay 60. When this orientation is employed the portions can be disengaged from one another for introduction of a hydrating fluid in hydrating fluid bay 60, and can be reengaged with one another to allow the hydration process to proceed. As yet another embodiment (not shown), hydrating device 14 can be composed of three or more separable portions, which can be separated to access the material holding area 50 and hydrating fluid bay 60.

Figure 6:
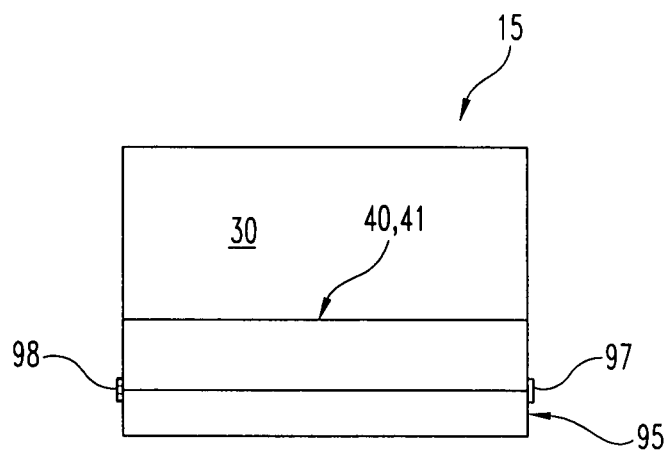
FIG. 6 is a diagrammatic front elevation view of another embodiment of a hydration device in accordance with the present application.

Fasteners 97, disposed above bottom portion 95 of the second portion 22, are operable to fasten portions 21 and 22 together in an engaged orientation for use of hydration device 14, and to be disengaged for separation of portions 21 and 22 from one another. Hinge 98 depicted in FIG. 6 can optionally be included in other embodiments. Gasket 96 is optionally present to provide improved sealing when portions 21 and 22 are engaged together. Gasket 96 can be, for example, an o-ring seal or other seal as would occur to a person of ordinary skill in the art.

The present application contemplates that the material to be hydrated can take a wide variety of different forms. In particular, devices provided by the present application are useful for the hydration and rehydration of a wide variety of different orthopedic graft materials such as, but not limited to, allograft materials (e.g., human-based graft materials), xenograft materials (e.g., non-human or animal-based graft materials), and synthetic materials (e.g., ceramic graft materials such as calcium-based materials, calcium-phosphate-based materials, calcium-sulfate-based materials, calcium-sodium-phosphate-based materials, as well as many others). Exemplary of materials that can be hydrated using methods, devices and principles described herein are an absorbable collagen sponge (ACS), a MasterGraft Matrix and a MasterGraft Putty. Various orthopedic graft materials, especially the synthetic materials, can be shaped into a wide variety of configurations, including but not limited to blocks, rings, struts, machined shapes, chips, granules and pastes. As will be appreciated by persons of ordinary skill in the pertinent art, one type of material that is commonly hydrated just prior to use is a flowable material. Such a material can be injected through a cannula or other conduit into an in vivo location. As used herein, the term "flowable" refers to a characteristic of a material whereby, after it is hydrated, it can be passed through a conduit by exerting a hydraulic pressure in the conduit. Examples of flowable materials include powdered ceramic cements such as, for example, tetracalcium phosphate/tricalcium phosphate cement, calcium sodium phosphate cement, and calcium sulfate. The powder portion would typically be mixed with a citric acid solution or a citrate salt solution to form a thick paste which hardens after a period of time typically ranging up to 20 or 30 minutes.

The hydrating fluid used to hydrate materials in accordance with the present application can be pure water or can be any number of aqueous-based liquids, such as saline, blood, bone marrow, reconstituted recombinant protein solutions or the like. Moreover, the hydrating fluid can include biologically active agents (e.g., therapeutic and/or prophylactic) such as, for example, antibiotics, platelet concentrates, bone growth factors or the like. In one embodiment, the hydrating fluid includes rhBMP-2.

Figure 7:
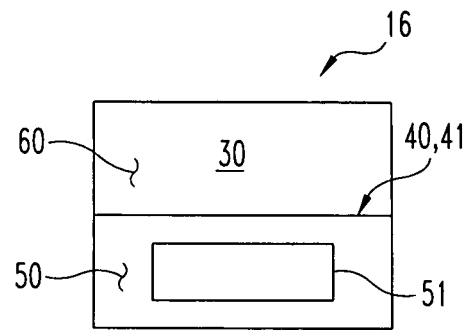
FIG. 7 is a diagrammatic front elevation view of another embodiment of a hydration device in accordance with the present application.
Figure 8:
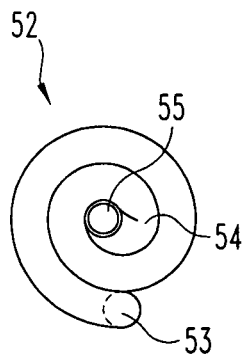
FIG. 8 is a top view of a coil-shaped embodiment of a delivery device in accordance with the present application.
Figure 9:
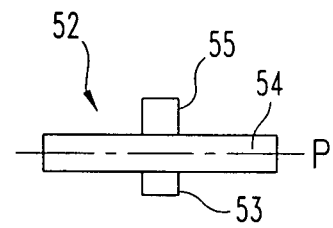
FIG. 9 is a diagrammatic front elevation view of the coil-shaped delivery device embodiment depicted in FIG. 8.
Figure 10:
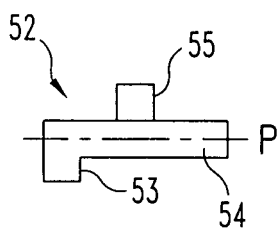
FIG. 10 is a diagrammatic side elevation view of the coil-shaped delivery device embodiment depicted in FIG. 8.

In one manner of using a flowable material in accordance with the present application, a flowable material to be hydrated is contained in a delivery device 51, as depicted in FIG. 7, and delivery device 51 containing the flowable material is placed in hydration device 11, 12, 13, 14, 15, 16 for the material to by hydrated. After the material is hydrated, delivery device 51 containing the hydrated material is removed from the hydration chamber and used to deliver the material to a desired in vivo location. One example of such a delivery device is coil-shaped delivery device 52 shown in FIGS. 8-11. Device 52 includes a coiled tubular conduit 54 that forms a generally planar coil in plane P. First end 53 of conduit 54 is located at an outer edge of the coil. First end 53 can open in a direction in plane P or in a direction outside of plane P. In the embodiment depicted in FIGS. 8-11, end 53 opens in a direction that is perpendicular to plane P. A second end 55 of conduit 54 is located at a central part of the coil, and second end 55 opens in a direction outside of plane P. In the embodiment depicted in FIGS. 8-11, second end 55 opens in a direction that is perpendicular to plane P and that is opposite of the direction to which first end 53 opens. Some or all of delivery device 52 is composed of a permeable material that allows passage of a hydrating fluid therethrough. As such, when a material to be hydrated is placed in device 52, device 52 is placed in material holding area 50, and a hydrating fluid is introduced into hydrating fluid bay 60, the fluid passes from bay 60, through barrier 40, 41 into area 50, and then through the permeable material of device 52 and into contact with a material to be hydrated contained therein. After the material contained therein is fully hydrated, device 52 can be removed from area 50 for delivery of the material to an in vivo location, as described further below.

With reference to FIG. 16, each of first and second ends 53 and 55 of delivery device 52 is configured for attachment to a conduit. In the embodiment depicted in FIG. 16, first end 53 of coiled delivery device 52 is attached to proximal end 203 of delivery conduit 202. Distal end 204 of conduit 202 can be placed at an in vivo location to which delivery of the material contained in device 52 is desired. Second end 55 of device 52 is connected to proximal end 206 of conduit 205. Distal end 207 of conduit 205 is connected to a source 201 of hydraulic pressure such as, for example, a syringe. When source 201, conduit 205, device 52 and delivery conduit 202 are operably connected as described, hydraulic pressure from source 201 is transmitted through conduit 205 to end 55 of device 52, which forces the flowable, hydrated material from tubular conduit 54 into delivery conduit 202. Further application of pressure causes the hydrated material to exit end 204 of delivery conduit to a desired in vivo location. In alternative embodiments, conduit 205 can be absent, in which case hydraulic pressure source 201 can be connected directly to end 55 of device 52. In addition, the present application contemplates that device 52 can alternatively be fluidly connected to delivery tube 202 and pressures source 201 in the opposite orientation, i.e., such that pressure source 201 is operably connected to end 53 of device 52 and delivery tube 202 is operably connected to end 54 of device 52. The application also contemplates that one or both of ends 53 and 55 can include caps, plugs or valves (not shown) for preventing the premature exit of flowable material from device 52. In addition, conventional connectors (not shown) such as, for example, Luer connectors, can be employed as would occur to a person of ordinary skill in the art, for joining ends 53, 55 of device 52; ends 203, 204 of tube 204; ends 206, 207 of tube 205; and source 201.

Figure 11:
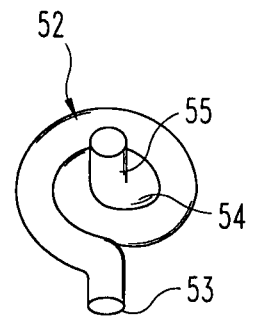
FIG. 11 is a front perspective view of the coil-shaped delivery device embodiment depicted in FIG. 8.
Figure 11A:
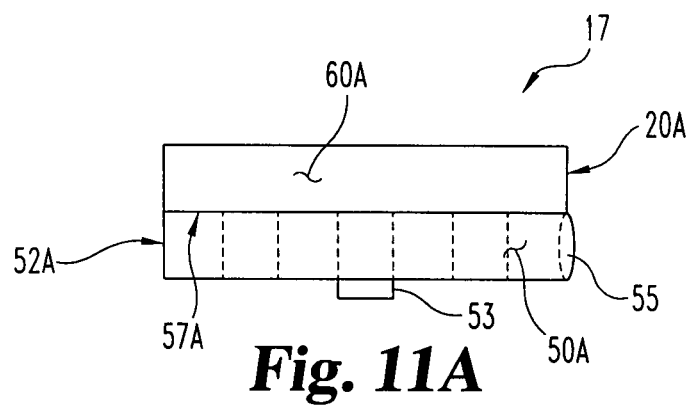
FIG. 11A is a diagrammatic front elevation view of another embodiment of a coil-shaped delivery device in accordance with the present application.

In another embodiment, depicted in FIG. 11A, coiled delivery component 52A configured similarly to device 52 forms the material holding area 50A of hydration device 17 and operates as a material delivery vehicle after hydration of the material contained within tube 54. In such an embodiment, component 20A defining hydrating fluid bay 60A is sealingly affixed to coiled component 52A adjacent first side 57A of coiled component 52A, resulting in a configuration where first side 57A of component 52A operates a barrier similar to barrier 41 between bay 60A and material holding area 50A (i.e., the interior of the tube that forms coil component 52A). First side 57A of coiled component 52A in this embodiment is composed of a permeable material that allows hydrating fluid to pass therethrough from hydrating fluid bay 60A into the material holding area 50A and into contact with a material contained therein. After the material is hydrated, a hydraulic pressure source (not shown) and a delivery tube (not shown) can be connected to ends 53, 55 of component 52A for delivery of the flowable material to an in vivo location as described above in connection with device 52.

Figure 11B:
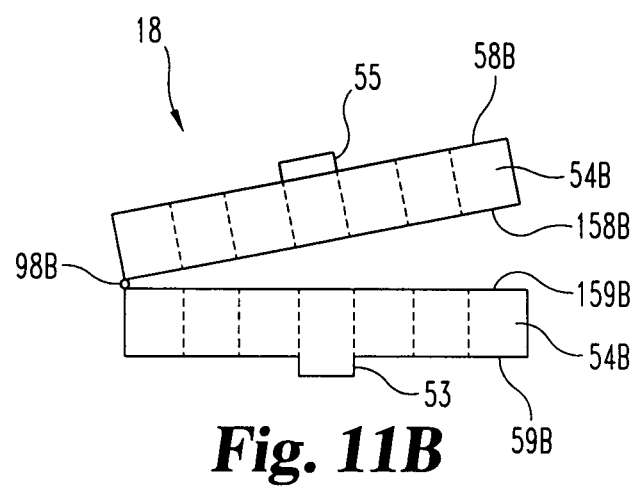
FIG. 11B is a diagrammatic front elevation view of another embodiment of a coil-shaped delivery device in accordance with the present application.

In another embodiment, depicted in FIG. 11B, the coiled component itself can be divided into two halves in a manner whereby the coiled tube 54B is divided along its length into a first half 58B and a second half 59B. By separating halves 58B 59B, device 18 can be loaded with a material to be hydrated, and can optionally also be loaded with a hydrating fluid to initiate the hydration process and then closed with halves 58B, 59B sealingly engaged to one another. The halves 58B, 59B, when sealingly engaged, form a coil-shaped conduit from which the material can be expressed after hydration is complete. As will be appreciated, the two halves 58B, 59B can optionally be connected by hinge 98B, and various mechanisms known in the art can be employed to ensure that the halves form a good seal at each point of connection along coiled tube 54B. Such sealing can be achieved, for example, using gasket seals (not shown) configured to be positioned between inner edges 158B, 159B of halves 58B and 59B.

In another alternative embodiment, a hydration and material delivery device includes a material holding area formed as a spiral shaped coil, positioned within a container. The space within the container and external to the coil operates as a hydrating fluid bay. The coil can be formed of a permeable material such that introduction of a hydrating fluid into the hydrating fluid bay results in passage of the fluid into contact with a flowable material to be hydrated that is contained in the material holding area within the coil. After the material is hydrated, it can be expressed from the coil in a manner similar to that described above in connection with device 52.

In another embodiment a delivery device is a generally straight tube rather than a coiled tube. For example, one or more generally straight tubes containing one or more materials to be hydrated can be placed in material holding area of device 10, 11, 12, 13, 14, 15, 16 for hydration, and the hydrated material can be expressed from the tubes in a manner similar to that described above in connection with coiled delivery device 52. Straight tubes can optionally include caps or plugs at each end to keep a flowable material from prematurely exiting the tube, and some or all of the tube can be composed of a permeable material to allow a hydrating fluid to enter the tube to come into contact with a material to be hydrated contained therein.

In yet another embodiment, a generally straight tube containing a material to be hydrated can itself form part of a hydrating device. For example, with reference to FIG. 12, device 110 includes barrier 140 that defines internal hydrating fluid bay 160 and extends in a probe-like manner into material holding area 150. Device 110 further includes connection port 180 and optional engaging means, such as threads (not shown) for attaching a hydrating fluid source (not shown) to port 180. In one embodiment, barrier 140 has a tubular shape. Barrier 140 can be composed of a permeable material or can be formed of an impermeable material that has one or more apertures formed therethrough for allowing passage of a hydrating fluid from bay 160 into area 150. In one embodiment barrier 140 includes a first portion 162 that is impermeable to the hydrating fluid and a second portion 164 that allows passage of the hydrating fluid. In another embodiment, barrier 140 is rotatably connected to container body 120. An embodiment with a rotatable barrier 140 affords the user a degree of control over the hydration process. For example, this embodiment finds excellent use in circumstances where it is desirable to hydrate more than one diverse materials in a certain order using a single device, to hydrate a bi-phasic material, or to hydrate one portion of a material more thoroughly than one or more other portions. In such circumstances, an embodiment of device 110 having a first impermeable portion 162 and a second portion 164 that allows passage of the hydrating fluid can be used to first hydrate a material positioned in a first portion of material holding area 150 at a first side of probe-shaped barrier 140. After a predetermined period of time, barrier 140 can be rotated, thereby reorienting portion 164 to a position adjacent a second portion of material holding area 150 for hydration of a material positioned at the second location. In alternate embodiments, material holding area 150 can include partitions (not shown) for separating different portions, or can omit partitions.

In one excellent manner of using device 110, hydrating fluid is infused from a hydrating fluid source (not shown) into hydrating fluid bay 160 through port 180, and then bay 160 is pressurized to pass the fluid through barrier 140 into material holding area 150. Pressurization of bay 160 can be achieved in a wide variety of ways, including, for example using devices and techniques described in connection with device 13 shown in FIG. 4. In addition, as described above in connection with device 13, device 110 can include one or more optional valves similar to valve 90, and can optionally include end cap 122 or other separable portion as described in connection with device 14 depicted in FIG. 5. In certain embodiments, barrier 140 is removable, and can advantageously be removed after hydration of a material in area 150 for easier removal of the material from container 120. Moreover, barrier 140 can be initially provided separated from container 120 for subsequent insertion after a material to be hydrated is positioned in area 150. Barrier 140 can be affixed to container 120 in a wide variety of ways as would occur to a person of ordinary skill in the art.

In some uses of device 110, the material being hydrated is a flowable material that can be expressed from area 150 through a tube and into an in vivo location in a manner similar to that by which hydrated material is expressed from coiled delivery device 52. In one representative example of a manner of expressing material from device 110, barrier 140 is removed and port 180 is connected to proximal end 206 of conduit 205 depicted in FIG. 16. Distal end 207 of conduit 205 is connected to a source 201 of hydraulic pressure such as, for example, a syringe, as shown in FIG. 16 for device 52. In addition, optional cap 122 is removed and end 153 of device 110 is attached to proximal end 203 of delivery conduit 203. As described in connection with FIG. 16, distal end 204 of tube 202 can be placed at an in vivo location to where delivery of the material contained in device 110 is desired. When source 201, conduit 205, device 110 and delivery conduit 202 are operably connected as described, hydraulic pressure from source 201 is transmitted through conduit 205, through port 180 to area 150 of device 110, which forces the flowable, hydrated material from area 150 into delivery conduit 202. Further application of pressure causes the hydrated material to exit end 204 of delivery conduit to a desired in vivo location. In alternative embodiments, conduit 205 can be absent, in which case hydraulic pressure source 201 can be connected directly to port 180 of device 110. In addition, the present application contemplates that device 110 can alternatively be fluidly connected to delivery tube 202 and pressures source 201 in the opposite orientation, i.e., such that pressure source 201 is operably connected to end 153 of device 110 and delivery tube 202 is operably connected to port 180. As described above in connection with the assembly depicted in FIG. 16, conventional connectors (not shown) such as, for example, Luer connectors, can be employed as would occur to a person of ordinary skill in the art, for making the necessary connections.

Another alternative hydrating device embodiment 111 is depicted in FIG. 13. Device 111 is a cartridge defining multiple chambers 124, each of which includes a connection port 180, a material holding area 150 and a hydrating fluid bay 160. FIG. 14 shows a cross-sectional view of device 111 taken at line 14-14 of FIG. 13. Any one or more of chambers 124 can have one or more additional features as described above in connection with device 110. In the embodiment shown in FIG. 13, a chamber plug 126 is provided for each of chambers 124. Plug 126 is configured for sealing engagement with cartridge 111 and can be provided with threads (not shown) or other means of engaging cartridge 111. In alternate embodiments, cartridge 111 can be formed to received caps or other sealing components.

Figure 17:
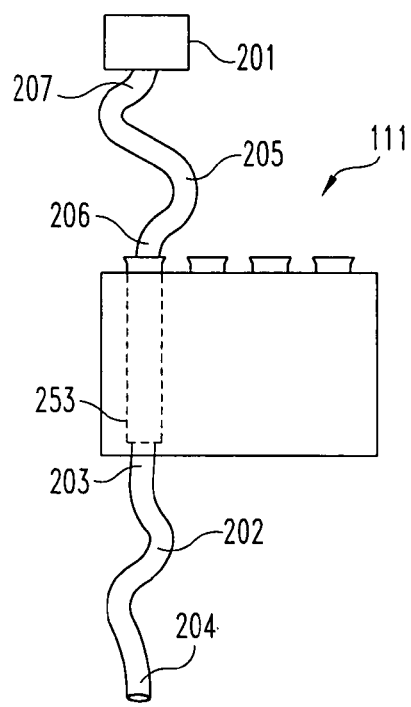
FIG. 17 depicts another assembly for delivering a flowable hydrated material to an in vivo location in accordance with the present application.

In operation, a material to be hydrated is positioned in one or more of areas 150. The same material can be positioned in multiple chambers or different materials can be placed in one or more different chambers. When one or more material is contained therein, device 111 preferably includes labels or other indicia on its external surface identifying the material in each chamber. A selected hydrating fluid appropriate for hydrating a material contained in a certain chamber is introduced into the hydrating fluid bay of the respective chamber from a hydrating fluid source (not shown) through the port 180 corresponding to the chamber. After a material contained in area 150 has been hydrated, plug 126 (or cap or other sealing component, if present) corresponding to the respective chamber 124 can be removed for attachment of a delivery tube, such as tube 202 as shown in FIG. 17. In addition, barrier 140 can optionally be removed and port 180 is connected to proximal end 206 of conduit 205. Distal end 207 of conduit 205 is connected to a source 201 of hydraulic pressure such as, for example, a syringe. Distal end 204 of tube 202 can be placed at an in vivo location to where delivery of the material contained in device 111 is desired. When source 201, conduit 205, device 111 and delivery conduit 202 are operably connected as described, hydraulic pressure from source 201 is transmitted through conduit 205, through port 180 to area 150 of device 111, which forces the flowable, hydrated material from area 150 into delivery conduit 202. Further application of pressure causes the hydrated material to exit end 204 of delivery conduit to a desired in vivo location. In alternative embodiments, conduit 205 can be absent, in which case hydraulic pressure source 201 can be connected directly to port 180 of device 111. In addition, the present application contemplates that device 111 can alternatively be fluidly connected to delivery tube 202 and pressures source 201 in the opposite orientation, i.e., such that pressure source 201 is operably connected to end 253 of chamber 124 and delivery tube 202 is operably connected to port 180. Conventional connectors (not shown) such as, for example, Luer connectors, can be employed as would occur to a person of ordinary skill in the art, for making the necessary connections. Alternatively, other systems can be attached to device 111 for expressing the hydrated material from area 150 to an in vivo location, additional examples of which are discussed below.

In another multiple-chamber cartridge embodiment depicted in FIG. 15, device 112 includes multiple chambers 124, each of which includes a material holding area 150 and a hydrating fluid bay 160. Device 112 further includes a manifold hydrating fluid chamber 161 in fluid communication with each of hydrating fluid bays 150 and with connection port 180. In the embodiment shown in FIG. 15, a chamber cap 127 is provided for each of chambers 124. Cap 127 is configured for sealing engagement with cartridge 112 and can be provided with threads (not shown) or other means of engaging cartridge 112. In alternate embodiments (not shown) cartridge 112 can be formed to received plugs (as described in connection with device 111) or other sealing components. Any one or more of chambers 124 can have one or more additional features as described above in connection with devices 110 and 111.

In operation, a material to be hydrated is positioned in one or more of areas 150. The same material can be positioned in multiple chambers or different materials can be placed in one or more different chambers; however, it is to be understood that if different materials are to by hydrated together in device 112, the materials should be of a type that are hydratable with the same fluid. As described above in connection with device 111, when one or more material is contained therein, device 112 preferably includes labels or other indicia on its external surface identifying the material in each chamber. A selected hydrating fluid appropriate for hydrating the materials contained in the one or more chambers is introduced into the manifold space 161 from a hydrating fluid source (not shown) through port 180. After entering manifold space 161, the fluid flows into hydrating fluid bays 160, through barriers 140 and into contact with the material(s) contained in material holding areas 150. After a material contained in area 150 has been hydrated, cap 127 (or plug or other sealing component used) can be removed for attachment of a delivery tube, such as tube 202 as shown in FIG. 17. In addition, port 180 is connected to proximal end 206 of conduit 205. Distal end 207 of conduit 205 is connected to a source 201 of hydraulic pressure such as, for example, a syringe. Distal end 204 of tube 202 can be placed at an in vivo location to which delivery of the material contained in the respective chamber 124 of device 112 is desired. When source 201, conduit 205, device 112 and delivery conduit 202 are operably connected as described, hydraulic pressure from source 201 is transmitted through conduit 205, through port 180 and manifold space 161, to bays 160. This pressure transfers across barrier 140 to area 150 of device 112 and forces the flowable, hydrated material from area 150 into delivery conduit 202. Further application of pressure causes the hydrated material to exit end 204 of delivery conduit to a desired in vivo location. In alternative embodiments, conduit 205 can be absent, in which case hydraulic pressure source 201 can be connected directly to port 180 of device 112. Conventional connectors (not shown) such as, for example, Luer connectors, can be employed as would occur to a person of ordinary skill in the art, for making the necessary connections.

When using device 112, if only one of caps 127 has been replaced with a delivery tube, such as delivery tube 202 depicted in FIG. 17, material from the corresponding chamber will be expressed into the delivery tube. Thereafter, the pressure can be released, the delivery tube detached, the cap replaced, and the delivery tube can be connected to a second chamber. The application of pressure again into manifold space 161 will then cause a flowable material contained in the second chamber to be expressed therefrom in a similar fashion. This process can be repeated as many times as necessary or as desired to express material from multiple chambers of device 112.

Figure 18:
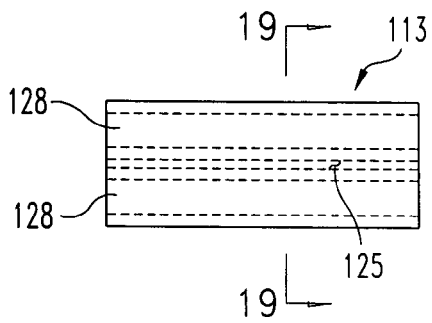
FIG. 18 is a front elevation view of another embodiment of a hydration device in accordance with the present application.
Figure 19:
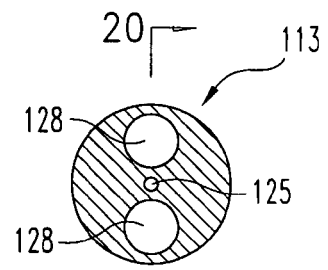
FIG. 19 is a cross section view of the embodiment depicted in FIG. 18, taken along line 19-19.
Figure 20:
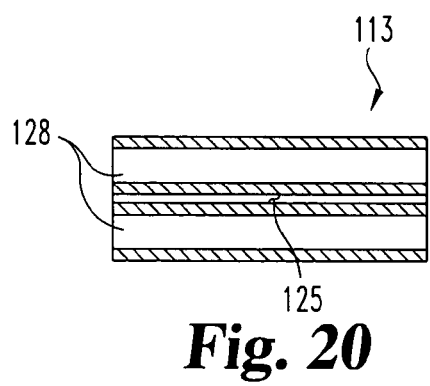
FIG. 20 is a cross section view of the embodiment depicted in FIGS. 18 and 19, taken along line 20-20.
Figure 21:
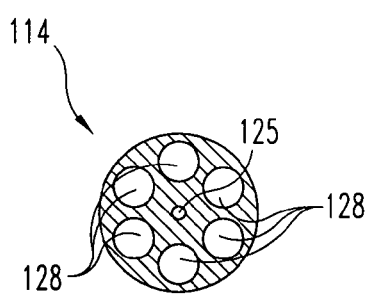
FIG. 21 is a cross section view of another embodiment of a hydration device in accordance with the present application.

Another embodiment of a multi-chamber cartridge is depicted in FIGS. 18-20. Device 113 is configured as a revolving cartridge that defines first and second hydration chambers 128. A cross-sectional view of cartridge 113 along line 19-19 in FIG. 18 is depicted in FIG. 19, and a longitudinal cross-section along line 20-20 in FIG. 19 is set forth in FIG. 20. Device 113 can optionally include one or more ports (not shown) operably associated with chambers 128, such as ports 80, 180 depicted in FIGS. 4, 12, 13 and 15; can optionally include probe-shaped barriers (not shown) such as barrier 140 depicted in FIGS. 12-15; can optionally include Luer connectors (not shown) at one or both ends of chamber 128; and can optionally include caps, plugs or other sealing means (not shown) such as cap 127 or plug 126 depicted in FIGS. 15 and 13, respectively. Moreover, more than two hydration chambers can be included. For example, device 114 depicted in FIG. 21 includes six hydration chambers 128, and is therefore operable to hydrate six quantities of material for use in a single medical procedure.

A hydrated material positioned in one or both of chambers 128 of device 113 can be expressed therefrom using tubes and a hydraulic fluid source in the manner described above in connection with coiled delivery device 52, tubular device 110, and multi-chamber cartridge devices 111 and 112. Alternatively, revolving cartridge 113 can be configured for engagement with a delivery tool (also referred to herein as an "expresser device") for expressing hydrated materials from one or more of chambers 28 to an in vivo location.

In another aspect of the present application, there is provided a device for delivering a flowable, hydrated material to an in vivo location. The device is configured to releasably engage a container body defining therein a chamber with a flowable, hydrated material contained in the chamber. The device is operable to express the material from the chamber. In some embodiments, the device also includes a delivery tube operable to receive the material after it is expressed from the chamber and to carry the material to an in vivo location. In one representative embodiment, the device includes a retaining member configured to releasably engage a container body defining therein one or more chamber with a flowable, hydrated material contained therein, an expresser component that is operable to express the material from the chamber, and a conduit that is operable to receive the material after it is expressed from the chamber.

Figure 22:
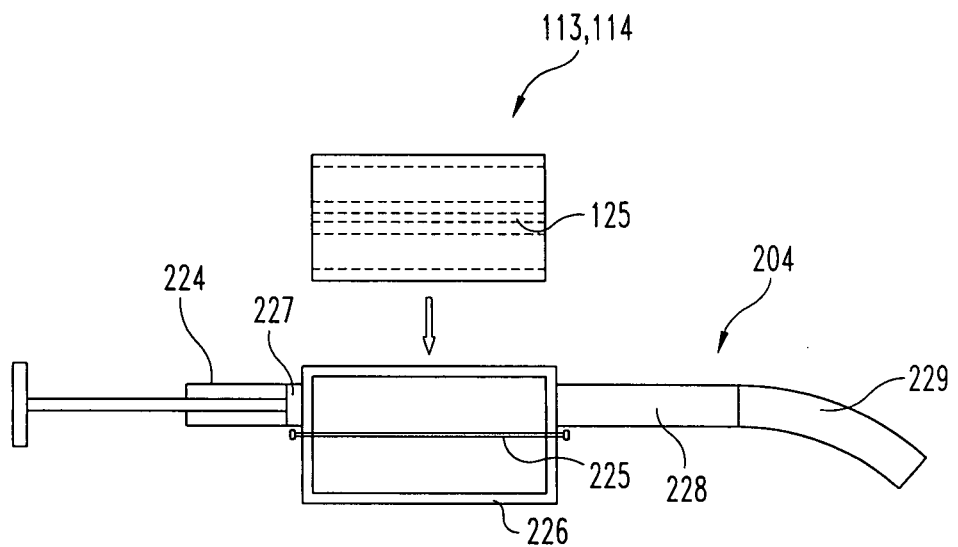
FIG. 22 depicts another assembly for delivering a flowable hydrated material to an in vivo location in accordance with the present application.

With reference again to FIGS. 18-22, devices 113, 114 optionally include central channel 125 for receiving an axle upon which cartridge 112 can rotate. With reference now to FIG. 22, delivery device 204 includes retaining member 226 that retains axle 225. Axle 225 is configured to be received in central channel 125 of cartridge 113, 114 to rotatably and releasably attach cartridge 113, 114 to device 204. Device 204 further includes material delivery conduit 228 and plunger 227 that is slidably held by plunger guide 224. Flexible or semi-rigid tube 229 is optionally attached to conduit 228. In certain embodiments, tube 229 and optional conduit 228 (if present) have an internal diameter (referred to as the second diameter) similar to the internal diameter of chambers 128 and/or tubular material holding areas 150 with which device 204 is configured to be used (referred to as the first diameter). In some applications it is desirable for the assembled container body and delivery device to be operable to deliver a material having a viscosity of from about 700 to about $1.0 \times 10^8$ centi-Poise (cP) at a temperature of from about 22° C. to about 25° C. In one embodiment, the second diameter is within a range that is no more than 50% larger or smaller than the first diameter. In another embodiment, the second diameter is within a range that is no more than 30% larger or smaller than the first diameter. In yet another embodiment, the second diameter is substantially the same as the first diameter.

In operation, after a flowable material residing in one or more of hydration chambers 128 is hydrated, cartridge 113, 114 is operably attached to device 204 by positioning cartridge 113, 114 and inserting axle 225 into channel 125. When axle 225 is seated in channel 125, cartridge 113, 114 is held in a position whereby cartridge 113, 114 can be positioned to align one of chambers 128 with plunger 127 and conduit 228. In this position, manual operation of the plunger, i.e., pressing plunger into chamber 128 expresses the flowable hydrated material from chamber 128 and into conduit 228 for delivery to an in vivo location. After the material is expressed from the chamber, plunger is withdrawn from the chamber and cartridge 113, 114 can be rotated about axle 225 to align a second of chambers 228 with plunger 227 and conduit 228. In this position, material from the second chamber can be expressed as described. This series of operations can be repeated as many times as desired until the material has been expressed from each of chambers 128 or until a sufficient total amount of hydrated material has been expressed. If additional material is needed, of course, the revolving cartridge 113, 114 can be replaced with a second revolving cartridge having hydrated material therein for delivery of additional material.

The present application also contemplates that various components of delivery device 204 can be substituted with alternative configurations for achieving delivery of the hydrated material. For example, in an alternative embodiment (not shown) axle 225 can be substituted with retaining pins that are inserted only a short distance into channel 125. Moreover, when retaining pins are used, channel 125 can be replaced by shorter cavities in each end of cartridge 113, 114 at the longitudinal axis thereof to allow for rotation of cartridge 113, 114 about the pins. In additional plunger 227 and plunger guide 224 (referred to collectively herein as "expresser component") can be substituted with an alternative component for expressing the material from chamber(s) 128. For example, in one embodiment, the expresser component is a device for applying hydraulic pressure to the material in chamber 128 of device 113, 114. For example, device can include a Luer connection in place of plunger 227 so that a syringe fitted with a mating Luer connector can be attached to device 204 for application of hydraulic pressure from the syringe.

In other embodiments, device 204 is configured to engage either a tubular container holding a single quantity of hydrated material, such as, for example, device 110 depicted in FIG. 12, or a multi-chamber cartridge such as, for example, cartridge 111 depicted in FIGS. 13 and 14, in which chambers are oriented linearly with regard to one another. In these embodiments, retaining member 226 and axle 225 can be replaced with alternate engagement structures suitable for attaching a single-chamber device or a linearly-oriented multi-chamber cartridge to device 204 for expressing a hydrated material therefrom. The present application contemplates, for example, that a multi-chamber cartridge having linearly-oriented chambers can be slidingly attached to device 204. When the cartridge is operably connected to device 204, the cartridge is held in a position whereby one of material holding areas 150 is aligned with plunger 127 (or other expresser component) and conduit 228. In this position, operation of the expresser component expresses the flowable hydrated material from material holding area 150 and into conduit 228 for delivery to an in vivo location. After the material is expressed from the chamber, cartridge 111 can be slid to another position to align a second of material holding areas 150 with the expresser component and conduit 228. In this position, material from the second chamber can be expressed as described. This series of operations can be repeated as many times as desired until the material has been expressed from each of material holding areas 150. If additional material is needed, of course, the cartridge 111 can be replaced with a second cartridge having hydrated material therein for delivery of additional material.

Figure 23:
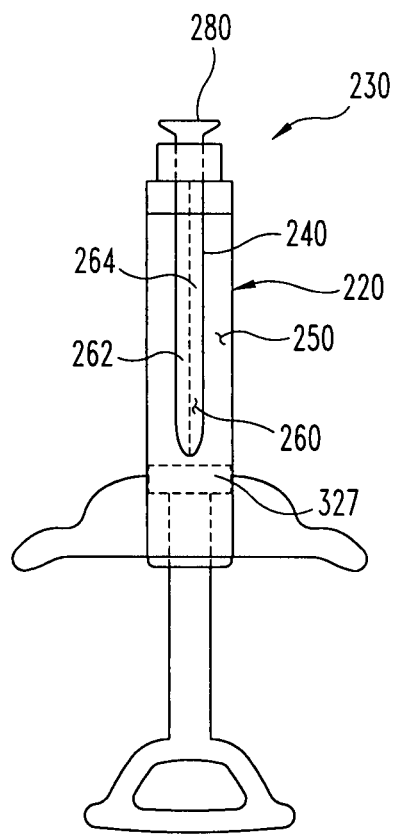
FIG. 23 is a front elevation view of another embodiment of a hydration device in accordance with the present application, which is also operable for delivering a flowable hydrated material to an in vivo location in accordance with the present application.

In another embodiment, a tubular hydration device is configured as a syringe-like material hydration and delivery device. With reference to FIG. 23, device 230 includes barrier 240 that defines internal hydrating fluid bay 260 and extends in a probe-like manner into material holding area 250. Device 230 further includes connection port 280 and optional engaging means, such as threads (not shown) for attaching a hydrating fluid source to port 280. In one embodiment, barrier 240 has a tubular shape. Barrier 240 can be composed of a permeable material or can be formed of an impermeable material that has one or more apertures formed therethrough for allowing passage of a hydrating fluid from bay 260 into area 250. In one embodiment barrier 240 includes a first portion 262 that is impermeable to the hydrating fluid and a second portion 264 that allows passage of the hydrating fluid. In another embodiment, barrier 240 is rotatably connected to syringe body 220. As described above, an embodiment with a rotatable barrier 240 affords the user a degree of control over the hydration process. For example, this embodiment finds excellent use in circumstances where it is desirable to hydrate more than one diverse materials in a certain order using a single device, to hydrate a bi-phasic material, or to hydrate one portion of a material more thoroughly than others. In such circumstances, an embodiment of device 230 having a first impermeable portion 262 and a second portion 264 that allows passage of the hydrating fluid can be used to first hydrate a material positioned in a first portion of material holding area 250 at a first side of probe-shaped barrier 240. After a predetermined period of time, barrier 240 can be rotated, thereby reorienting portion 264 to a position adjacent a second portion of material holding area 250 for hydration of a material positioned at the second location.

In one excellent manner of using device 230, hydrating fluid is infused from a hydrating fluid source (not shown) into hydrating fluid bay 260 through port 280, and then bay 260 is pressurized to pass the fluid through barrier 240 into material holding area 250. Pressurization of bay 260 can be achieved in a wide variety of ways, including, for example using devices and techniques described in connection with device 13 shown in FIG. 4. In addition, as described above in connection with device 13, device 230 can include one or more optional valves similar to valve 90. In certain embodiments, barrier 240 is removable, and can advantageously be removed after hydration of a material in area 250 to facilitate expression of the material from syringe 220. Moreover, barrier 240 can be initially provided separated from syringe 220 for subsequent insertion after a material to be hydrated is positioned in area 250. Barrier 240 can be affixed to syringe 220 in a wide variety of ways as would occur to a person of ordinary skill in the art.

In some uses of device 230, the material being hydrated is a flowable material that can be expressed from area 250 through a tube and into an in vivo location in a manner similar to that by which hydrated material is expressed from other delivery devices described herein. In one representative example of a manner of expressing material from device 230, barrier 240 is removed and port 280 is connected to a proximal end of a delivery tube. The distal end of the delivery tube can be placed at an in vivo location to where delivery of the material contained in device 230 is desired. Hydraulic pressure can be exerted on area 250 by depressing plunger 327 of syringe 230. Hydraulic pressure from plunger 327 is transmitted to area 250 of device 230, which forces the flowable, hydrated material from area 250 into the delivery tube. Further application of pressure causes the hydrated material to exit the distal end of the delivery conduit to a desired in vivo location.

A hydration device in accordance with the present application can be used as a disposable, single-use device. Alternatively, some embodiments are configured such that they can be reusable. For example, embodiments that are configured to allow for thorough cleaning, sanitizing and reloading are ideal for re-use. For example, such embodiments can be returned to a manufacturer of the material to be hydrated for cleaning, sanitizing, reloading and packaging or, alternatively, they can be reloaded on-site. One aspect of the present application is a kit that includes a reusable hydration device as provided herein, a multi-use quantity of material to be hydrated and a multi-use quantity of hydrating fluid. Of course, the kit can also include one or more different materials and/or one or more different hydrating fluids, which enables medical personnel to prepare hydrated materials having desired features for a given use. In another aspect of the application, a kit is provided that includes a quantity of hydrating fluid and a hydration device as provided herein with a material to be hydrated already contained therein.

In another aspect, the application provides a packaged product that includes a container body defining therein a hydration chamber, an unhydrated medical material to be hydrated contained in the chamber and a removable seal operable to prevent passage of moisture into contact with the medical material. In one embodiment, the seal is positioned in the hydration chamber and separates the hydration chamber into a material holding area and a hydrating fluid bay, and the seal is operable to prevent passage of moisture from the hydrating fluid bay into the material holding area. For example, the product can be packaged in such a way that a hydrating fluid is contained in the hydrating fluid bay, and is kept from contacting the material by the seal positioned between the hydrating fluid bay and the material holding area. The product can also include a water permeable barrier as described above in connection with other embodiments, positioned in the hydration chamber adjacent the seal.

While multiple embodiments have been illustrated and described in detail in the drawings and foregoing description, the same is to be considered illustrative and not restrictive in character, it being understood that only selected embodiments have been shown and described and that all changes, equivalents, and modifications as would occur to those skilled in the art and that come within the scope of the inventions described herein or defined by the following claims are desired to be protected. Any experiments, experimental examples, or experimental results provided herein are intended to be illustrative of the present inventions and should not be construed to limit or restrict the scope of the present application. Further, any theory, mechanism of operation, proof, or finding stated herein is meant to further enhance understanding of the present application and is not intended to limit the inventions described herein in any way to such theory, mechanism of operation, proof, or finding. In addition, the various procedures, techniques, and operations may be altered, rearranged, substituted, deleted, duplicated, or combined as would occur to those skilled in the art. Further, any U.S. Patent, pending U.S. Patent Application Publication or other publication cited herein is incorporated herein by reference in its entirety as if each individual publication, patent, or patent application was specifically and individually indicated to be incorporated by reference and set forth in its entirety herein. In reading the claims, words such as the word "a," the word "an," the words "at least one," and the words "at least a portion" are not intended to limit the claims to only one item unless specifically stated to the contrary. Further, when the language "at least a portion" and/or "a portion" is used, the claims may include a portion and/or the entire item unless specifically stated to the contrary.

Any reference to a specific direction, for example, references to up, upper, down, lower, and the like, is to be understood for illustrative purposes only or to better identify or distinguish various components from one another. Any reference to a first or second vertebra or vertebral body is intended to distinguish between two vertebrae and is not intended to specifically identify the referenced vertebrae as adjacent vertebrae, the first and second cervical vertebrae or the first and second lumbar, thoracic, or sacral vertebrae. These references are not to be construed as limiting in any manner the medical devices and/or methods as described herein. Unless specifically identified to the contrary, all terms used herein are used to include their normal and customary terminology. Further, while various embodiments of medical devices having specific components and structures are described and illustrated herein, it is to be understood that any selected embodiment can include one or more of the specific components and/or structures described for another embodiment where possible.

What is claimed is:

1. A device for hydrating a medical implant material, comprising:
    a container body defining therein a hydration chamber; and
    a barrier extending from one side of the hydration chamber to an opposing side and separating the hydration chamber into a material holding area and a hydrating fluid bay,
    the barrier being porous and defining a plurality of capillary apertures through which the material holding area fluidly communicates with the hydrating fluid bay such that a hydrating fluid moves to the material holding area only by flowing through the plurality of capillary apertures,
    wherein said plurality of capillary apertures allow passage of the hydrating fluid from the hydrating fluid bay to the material holding area,
    wherein the device further comprises a removable seal effective to prevent passage of the hydrating fluid from the hydrating fluid bay to the material holding area, the removable seal extending from the one side of the hydration chamber to the opposing side adjacent to the barrier, the removable seal connected to a tab external to the container body, and the removable seal and the tab configured to be pulled entirely free from the device to allow for passage of the hydrating fluid to the material holding area,
    wherein the container body is composed of a rigid material, wherein the container body comprises first and second portions configured for alternate engagement with one another to form the hydration chamber, and disengagement from one another for removal of a material from the material holding area,
    the first and second portions being connected to one another by a hinge and a fastener,
    wherein the first and second portions are separable from one another.

2. The device in accordance with claim 1, wherein the barrier comprises a member selected from the group consisting of a permeable element, a screen and a fabric.

3. The device in accordance with claim 1, further comprising a connection port in fluid communication with the hydrating fluid bay, the port configured for engagement with a hydrating fluid source.

4. The device in accordance with claim 3, further comprising a valve in fluid communication with the material holding area.

5. The device of claim 3, further comprising a pressure applicator attachable to the port.

6. The device of claim 5, wherein the pressure applicator comprises a hydraulically-actuated piston or a hydraulically-inflatable bladder.

7. The device of claim 3, wherein the port is connected to a threaded fitting and a valve.

8. The device in accordance with claim 1, further comprising a gasket between the first and second portions to provide a seal when the first and second portions are in an engaged position.

9. The device in accordance with claim 1, further comprising a material to be hydrated contained in the material holding area; wherein the material to be hydrated is further contained in a delivery device.

10. The device of claim 1, wherein the rigid material is a plastic material.

* * * * *